United States Patent [19]

Mazza

[11] Patent Number: 4,871,682
[45] Date of Patent: Oct. 3, 1989

[54] DILUENT CARRYOVER CONTROL

[75] Inventor: John C. Mazza, El Toro, Calif.

[73] Assignee: Baxter Travenol Laboratories, Inc., Deerfield, Ill.

[21] Appl. No.: 106,018

[22] Filed: Oct. 1, 1987

Related U.S. Application Data

[63] Continuation of Ser. No. 858,217, Apr. 30, 1986, abandoned.

[51] Int. Cl.$^4$ .......................... G01N 1/14; G01N 21/11
[52] U.S. Cl. ...................................... 436/179; 436/49; 422/65; 422/100; 73/864.12
[58] Field of Search .................. 422/65, 100; 436/49, 436/179; 73/864.12

[56] References Cited

U.S. PATENT DOCUMENTS 4,574,850  3/1986  Davis .............................. 422/100 X
4,610,170  9/1986  Ekholm et al. ................. 436/179 X Primary Examiner—Barry S. Richman
Assistant Examiner—Lynn Kummert
Attorney, Agent, or Firm—Marjorie D. Hunter; Susan Fentress; Paul C. Flattery

[57] ABSTRACT

An air knife is positioned to direct a stream or blast of air across the tip of a sample probe as it is withdrawn from a cuvette containing a reagent, diluent, and patient sample solution. After the probe is flushed with diluent, the air knife drives any droplets of diluent fluid off the probe tip into the cuvette and thereby prevents contamination or dilution of the sample material in the sample containers.

10 Claims, 2 Drawing Sheets

DILUENT CARRYOVER CONTROL

This application is a continuation, of application Ser. No. 858,217, filed Apr. 30, 1986, now abandoned.

BACKGROUND OF THE INVENTION

This invention relates generally to the mixing of materials and to the analysis of the results of such mixing; to methods of and systems for the analysis of liquid biological samples; and to methods of and apparatus for mixing materials which are particularly suitable for mixing such a sample with a reagent to produce a reaction for analysis. In particular, the invention relates to methods of and apparatus for controlling the possibility of contaminating or diluting sample containers with wash diluent. The present invention is particularly useful in automated chemistry analyzers which are used for determining the presence and levels of one or more selected constituents in relatively small biological liquid samples.

Numerous automated clinical analyzers are known and widely used in hospital clinical laboratories. An example of such an analyzer is the multi-channel type analyzer.

A multi-channel analyzer is one in which a series of different tests are performed simultaneously by the analyzer, and in parallel with one another. Such an analyzer can be best visualized as a series of batch analyzers operating in parallel wherein each channel performs a single analysis test. The multi-channel type analyzer generally utilizes a liquid reagent to react with the particular constituent being tested in the sample and a photo-optical system to read the optical absorbance of the sample which corresponds to the level of the constituent in the sample.

Although this type of automated analyzer has received wide acceptance in the clinical laboratory, certain drawbacks are associated with its use. For example, although the multi-channel type analyzer is reliable due to its simplicity, cost effective for large number of samples and has a relatively high test throughput rate, it is limited in the sense that it can only be effectively utilized to perform a single constituent analysis at a time on a relatively large number of samples. In addition, such analyzers are not capable of performing emergency "stat" tests due to their relatively long and complex set up time and their inherent inability of economically analyze a single test sample.

A further significant disadvantage found is that although they can simultaneously perform tests for multiple constituents on the same sample, generally all of these tests must be performed for every sample whether desired or not. This results in a waste of both sample material and the reagents used in the unnecessary tests. Furthermore, due to the fact that multiple discrete and dedicated channels are utilized in such an instrument, there is significant duplication of numerous components which adds to the complexity and expense of the overall instrument.

An automated single track clinical analyzer which avoids the above-described in commonly owned U.S. patent application Ser. No. 284,840, filed July 20, 1981, now abandoned, entitled, "Automated Analysis Instrument System", the disclosure of which is hereby incorporated by reference in its entirety herein. By way of contrast to the multi-channel analyzer, the single track analyzer has both discrete and profile capabilities. The single track analyzer can perform different analytical profiled (i.e., profile analysis) or the same analytical test on a series of different patient samples (i.e., batch analysis). In either mode of the single track analyzer, the cuvettes containing samples are processed serially along a single track within the analyzer. The single track analyzer is capable of performing multiple selected tests on a single specimen and is adapted for handling "stat" testing of emergency samples and routine chemistries. To this end the analyzer is adapted to dispense different permutations of reagent and liquid biological sample into successive relatively small cuvettes advanced therethrough and has multiple analysis stations to which the cuvettes are fed in turn so that examination of the treated samples can be effected at varying time intervals without limiting the throughput of the instrument. These multiple analysis stations permit their positioning at read times that are closely related to theoretical optimal kinetic and endpoint reaction read times. Furthermore, by using a unique photo-optical system, also described in commonly owned U.S. patent application Ser. No. 284,841, filed July 20, 1981, now U.S. Pat. No. 4,477,190, entitled "Multichannel Spectrophoto- meter", the disclosure of which is hereby incorporated by reference in its entirety herein, greater flexibility of analysis at each analysis station is achieved. This is because the photo-optical system employs fiber optic bundles or similar light guides to transmit variable wavelengths of light to each analysis station from a single light source.

The single track analyzer utilizes a disposable cuvette belt formed from thin plastic film and defining a series of discrete reaction compartments (cuvettes) which are transported in line ahead through the instrument. The cuvettes are relatively small; they are generally for example capable of holding a final reaction volume of approximately 300 microliters. The patent sample in the cuvette is approximately 2020 microliters. Such a cuvette belt is described in commonly owned U.S. patent application Ser. No. 284,842, filed July 20, 1981, now abandoned, entitled, "Cuvette System For Automated Chemical Analyzers", the disclosure of which is incorporated in its entirety by reference herein. Such a belt provides handling flexibility and avoids the cross-contamination associated with flow-through cuvettes as well as avoiding the washing required of reusable cuvettes.

The earlier clinical analyzers discussed above employed liquid reagent, and mixing of the reagent with the diluent prior to addition of the biological sample was achieved by shooting a stream of the liquid reagent into the cuvette so as to produce a vortex-type mixing process. A preferred feature of the analyzer disclosed in U.S. patent application Ser. No. 284,840 is that it is adapted to utilize dry particulate reagents, preferably in tablet form, which are dispensed into the cuvettes from a rotating carousel which can hold a large number of doses. A preferred embodiment of tablet dispenser is described in commonly owned U.S. patent application Ser. No. 285,022, filed July 20, 1981, now U.S. Pat. No. 4,405,060, entitled, "Tablet Dispensing Device", the disclosure of which is hereby incorporated by reference in its entirety herein. In order to effect dissolution of the dry particulate reagent within the diluent prior to addition of the biological sample, the reagent and diluent are mixed by ultrasonic means.

A further advantageous feature of such an automated clinical analyzer is the use of microprocessor control, particularly for the dispensing and analysis station and the loading and transfer assembly for presenting to the analyzer containers having the samples to be tested.

A particular embodiment of the automated single track clinical analyzer according to aforesaid U.S. patent application Ser. No. 284,840 is the subject of the Paramax Analytical System manufactured by American Dade, a division of American Hospital Supply Corporation, of Miami, Fla. "Paramax" is a registered trademark of American Hospital Supply Corporation. In this system, which is under microprocessor control, a cuvette belt is cut into sections, comprising one or several cuvettes, which are fed in turn past a reagent tablet dispenser, a diluent dispenser, an ultrasonic horn for mixing the reagent and diluent, a sample dispenser and eight photo-optical analyzer stations. During their passage through dispensing and analysis, the cuvettes are supported in a water bath kept at a constant temperature and after analysis they pass through a sealing station and into a disposal station.

Reagent tablets are dispensed from a rotary carousel and the biological liquids to be sampled are delivered in tubes to the sample dispenser one at a time by a carousel having priority access positions to allow immediate "stat" sample entry. Codes on the tubes identify the samples and a code-reader alerts the microprocessor to operate the analyzer in accordance with the coded information. A further reagent dispenser is arranged between two of the analyzer stations for producing further sample reaction to permit additional analysis.

In the prior clinical analyzers as described above, the reagent and diluent are mixed in the cuvette prior to the addition of the liquid biological sample, either by shooting the reagent into the diluent to form a vortex in the case of a liquid reagent or by ultrasonic mixing in the case of the dry particulate reagent. Various improvements over such prior clinical analyzers have been disclosed in commonly owned U.S. application Ser. No. 575,924 filed Feb. 1, 1984, now abandoned entitled "Clinical Analysis Systems and Methods", the disclosure of which is incorporated herein in its entirety by reference.

It has been found, for example, that improved reliability and controllability of the analysis of the samples can be achieved by again mixing the contents of the cuvette after addition of the sample by directing an air jet to an acute angle against the surface of the liquid in the cuvette. Particularly good mixing is obtained where the air jet is directed at the liquid surface adjacent its junction wit the wall of the cuvette. The optimum point of contact of the air jet with the liquid surface has been found to be at the meniscus formed at the junction between the liquid surface and the wall of the cuvette.

The combination of directing the air jet against the liquid surface adjacent its junction with the wall of the cuvette and directing it at an acute angle to the surface producing a horizontal component has the beneficial effect of creating a vortex which produces a thorough mixing of the contents of the cuvette. Thus, a whirling or circular motion is induced in the contents tending to form a cavity of vacuum in the center and to draw the materials at the edge towards the center thus providing an effective mixing action. Particularly where the air jet hits the contents of the cuvette in the meniscus region, the contents tend to be raised up the wall of the cuvette opposite where the air jet hits the contents creating a particularly effective vortex producing very good mixing of the sample with the diluent and reagent. Thus a particulate reagent will become totally suspended within the diluent and the sample optimizing the reaction of the sample therewith.

By controlling the level of liquid in the cuvette and the air jet, splashing of the contents out of the cuvette leading to intercuvette contamination can be avoided. Splashing can, for example, be avoided by controlling the pressure of the air jet and/or by pulsing the air jet on and off.

The air jet may be directed at the liquid surface in the cuvette from a nozzle arranged inside the cuvette, but, in a preferred embodiment, the air jet is directed into the cuvette from outside the cuvette. Thus, a cuvette partially filled with the diluent, reagent and sample is disposed beneath an inclined nozzle and an air jet is directed at the liquid surface in the cuvette adjacent its junction with the wall of the cuvette from the nozzle.

In an automated system, the cuvette is partially filled to a predetermined liquid level and then advanced into alignment stationarily beneath a fixed nozzle so that the latter is aimed at the junction of liquid surface and cuvette wall. The angle of the air jet nozzle should ideally be as far as possible from the vertical providing maximum horizontal components of the air jet upon the liquid. The angle is determined by the diameter of the cuvette, the liquid level in the cuvette, which is itself controlled by the requirement to avoid splashing of the contents out of the cuvette, and the position of the nozzle over the mouth of the cuvette.

To obtain the optimum angle, the nozzle should be arranged diametrically opposite the point at which the air jet hits the liquid surface. Thus, in a preferred embodiment, the liquid level in the cuvette is suitable about 15 mm to about 25 mm below the mouth of the cuvette with the nozzle arranged to direct the air jet at an angle of between about 75 degrees and about 80 degrees to the liquid surface (horizontal), the cuvette being arranged vertically. When the cuvette has an elongated cross-section, the air jet is suitably aligned with the longer cross-sectional dimension.

The cuvette may be tilted towards the nozzle to permit the angle of the nozzle to be more horizontal.

It has been found that activation of the air jet for a period of between about 3.5 seconds, and about 4.5 seconds, preferably about 4 seconds, is usually sufficient to provide good mixing of the diluent, reagent and sample.

Numerous advantages are inherent in the apparatus and methods disclosed in the aforesaid application Ser. No. 575,924. It permits thorough mixing of the reagent, diluent and sample which enhances reliability and controllability of the test(s) of the sample. The mixing process occurs in a very fast timeframe. Intercuvette contamination is avoided by controlling the mixing action so hat splashing of material out of the cuvette is prevented. There is no physical contact between the nozzle and the contents of the cuvette and by having the nozzle arranged outside the cuvette, contamination of the nozzle is avoided and there is no need to move any component into the cuvette to effect the mixing, thus maximizing throughput in an automated process.

While it is preferred, particularly in an automated process, that the air-jet nozzle direct air into the cuvette from outside the cuvette, it is also possible to direct the air jet from inside the cuvette and aimed at the liquid surface from a position above the liquid surface. While requiring insertion and removal of the nozzle into and out of the cuvette (either by lowering and raising the nozzle or by raising and lowering the cuvette) this does have the advantage that the nozzle can be angled more closely to the horizontal without spilling of the contents. Thus, the nozzle may be inclined at an angle of between about 0 degrees to about 90 degrees to the horizontal, with the preferred embodiment of between about 8 and 15 degrees. Depending upon the height of the nozzle above the liquid surface, it may become contaminated by the liquid as it is agitated in which case it should be cleaned with diluent between mixing operations. It will be noted that in both instances, the nozzle is arranged above the liquid surface and is therefore noninvasive of the liquid.

Such an automated analyzer system may incorporate any or all of the features described in aforesaid U.S. patent application Ser. No. 284,840. Thus, a dry particulate reagent, preferably in tablet form, is dispensed into the cuvette together with a diluent and subject to ultrasonic mixing to effect dissolution of the reagent and dispersal in the diluent. A second, liquid reagent may be added at the same time as the diluent. The system has multiple analysis stations, having a photo-optical system as described in aforesaid U.S. patent application Ser. No. 284,841 to which the cuvettes are fed in turn. A further reagent dispenser is arranged between two of the analysis stations and a further mixing station, according to the invention, is arranged immediately following this dispenser which acts on each cuvette into which further reagent (preferably liquid) has been dispensed by directing an air jet against the liquid surface adjacent its junction with the cuvette wall to enhance further reaction of the sample.

SUMMARY OF THE INVENTION

In the course of the operation of the Paramax Analyzer System, a sample probe moves between one position to withdraw from a sample container a specimen of the sample material and another position to dispense the sample material into a cuvette already containing the reagent used in the analyzing process. In order to avoid contamination from cuvette to cuvette, the sample probe is kept well above the fluid in the cuvette when dispensing the sample material and the probe is washed with diluent after the sample is dispensed. However, the last drop or two of wash diluent does no drop off the probe end and is carried back to the sample container. Under such circumstances, these droplets tend to dilute the sample container, sometimes significantly, particularly if enough drops fall into the sample container during subsequent aspiration steps by the probe. To eliminate this potentially serious problem, an air knife is placed on the probe tip as the tip is lifted up out of the cuvette. The air knife drives any droplets of fluid off the probe tip before it is placed into a sample container. The air knife orifice is preferably elliptical in shape, the longest axis of the ellipse being placed parallel to the transport rail. The orifice is also carried down toward the mouth of the cuvette.

DESCRIPTION OF THE DRAWINGS

Other features and advantages of the present invention will become apparent from the following description taken in conjunction with the accompanying drawings wherein:

FIG. 5 is a plan view of the cuvette belt shown in FIG. 4;

FIG. 6 is a schematic side elevation of a mixing apparatus according to the invention of the clinical analyzer of FIG. 1;

FIG. 7 is an enlarged view of FIG. 6 showing the relationship of the mixing apparatus and the cuvette;

FIG. 8 is a plan view further illustrating the relation of the mixing apparatus and the cuvette;

FIG. 9 is a side view of a modified form of cuvette;

FIG. 10 is a schematic side elevation like that of FIG. 7 showing the mixing action produced when the apparatus is in use;

FIG. 11 is a schematic side elevation of a second embodiment of mixing apparatus according to the invention suitable for use in the clinical analyzer of FIG. 1;

FIG. 12 is a diagrammatic perspective view of air knife apparatus for driving off droplets of fluid from a sample probe;

FIG. 13 is an end elevation cross section view across the cuvette track, generally in the region of the sampler mechanism;

FIG. 14 is an enlarged detail view in elevation of parts illustrated in FIG. 13; and FIG. 15 is a detail cross section view taken generally along line 15—15 in FIG. 14.

DESCRIPTION OF THE PREFERRED EMBODIMENTS

Figure 1:
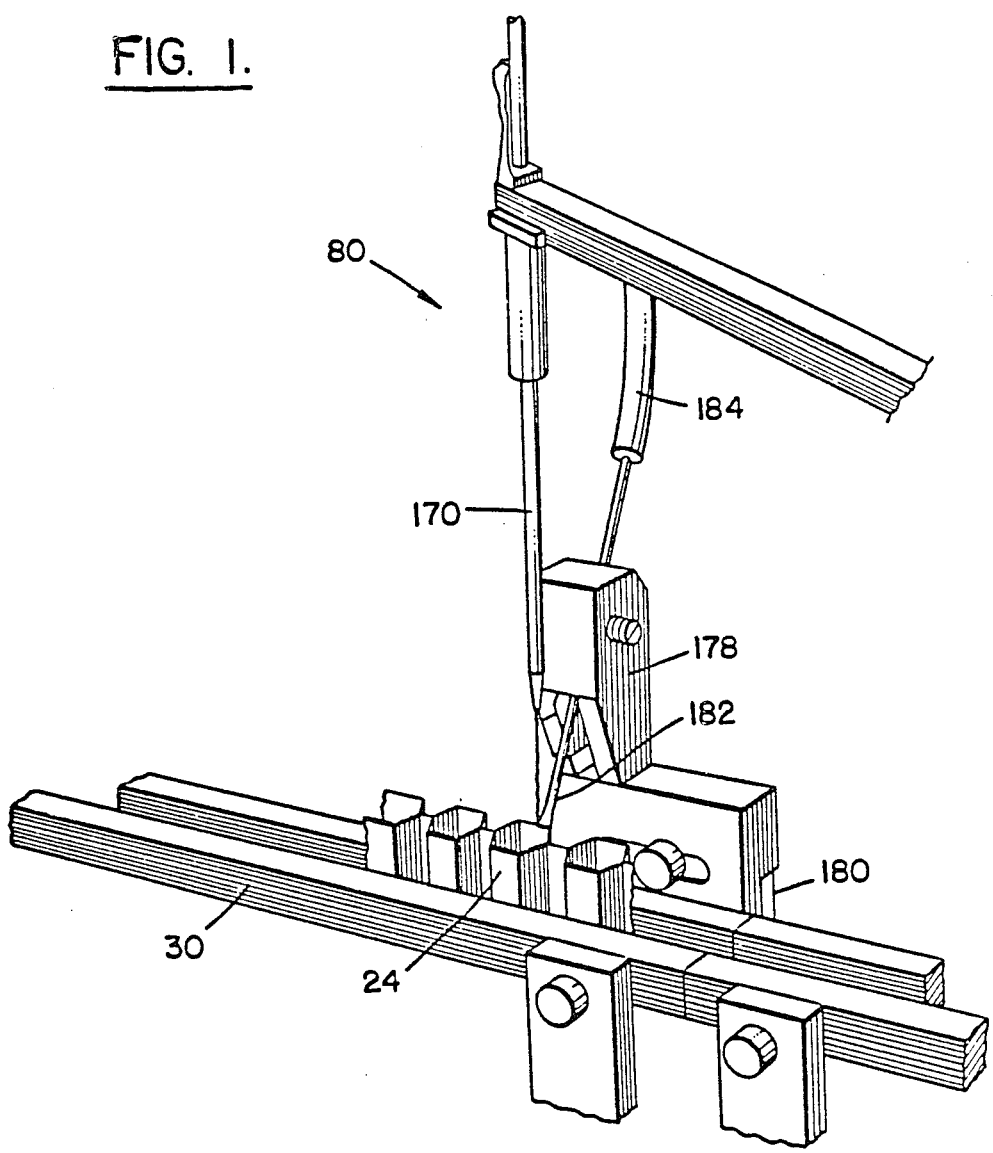
FIG. 1 is a schematic plan view of an automated clinical analyzer according to the present invention.
Figure 2:
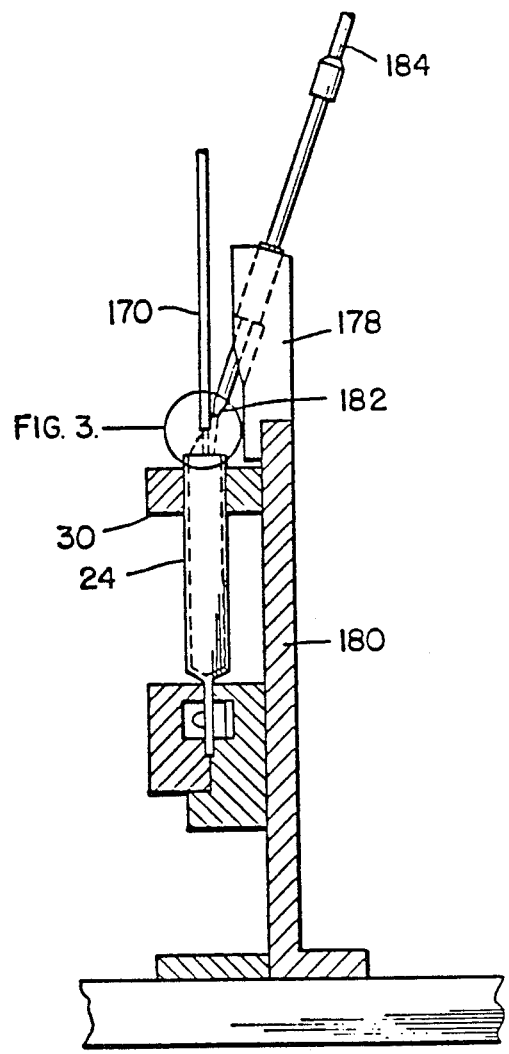
FIG. 2 is a partial perspective view of the automated clinical analyzer shown in FIG. 1.

FIG. 1 and 2 illustrate an automated clinical analyzer 10 generally as described in the aforesaid U.S. patent application No. 284,840 modified by the inclusion of mixing means in accordance with the present invention. More particularly, the analyzer is a modified Paramax Analytical System as manufactured by American Hospital Supply Corporation. The analyzer 10 is adapted for the testing of constituents in biological fluids, such as blood samples. The analyzer comprises a series of processing stations past which strips of disposable reaction cuvettes are indexed or advanced. The cuvettes 24 are supplied from a supply reel 20 as a continuous cuvette belt 22 and are indexed through the analyzer by tractor conveyor 30 which engages a row of index holes in the cuvette belt. The cuvettes are indexed in turn past the following stations: a belt cutter 28 for dividing the belt into sections; a tabletted reagent dispenser 40; a diluent and liquid reagent dispenser 50; an ultrasonic mixing horn 14; a sample dispenser 80 for dispensing biological samples delivered by a transfer carousel 64; an air-jet mixing apparatus 15 according to the invention for mixing the sample with the reagent and diluent in the cuvettes; eight photometric read stations 90; a further reagent dispenser 54; a further air-jet mixing apparatus 15a according to the invention for mixing the sample and the further reagent; a cuvette sealer 16 and a cuvette collection station 18. During their passage through the analyzer, the cuvettes are carried in a water bath 12 maintained at a constant temperature. These stations and their functions will now be described in detail.

The disposable cuvettes 24 are conveniently packaged in reels of as many as 2100 cuvettes. The belt 22 defined entirely separate reaction vessels designed to eliminate cross-contamination of reaction mixtures. The cuvette belt 22 is preferably constructed and made in the manner more fully described in aforesaid U.S. patent application Ser. No. 284,842 as will now be described briefly with particular reference to FIGS. 4 and 5.

The belt 22 comprises two strips 111, 112 of transparent plastics material which are moulded and sealed together to form a series of discrete, side-by-side parallel compartments (cuvettes) 24 separated by webs 115. The compartments are closed at one end and have an open mouth 117 at the other end so as to receive and retain fluid therein. For example, the cuvettes can be in the order of size so as to be capable of holding about 500 microliters of fluid. The compartments or vessels 24 are substantially rectangular in cross-section, being elongated along the length of the belt. They have generally parallel side faces 124 which define optical windows providing an optical path of precise length through each cuvette for accurate examination of the samples at the read stations 90. The flat web material 115 between the vessels 24 includes a transport strip portion extending alongside the closed ends thereof which is formed with indexing perforations or hole 26. These perforations are engaged by the tractor transport 30 of the analyzer 10 for conveying the cuvettes therethrough and maintaining a precise alignment of the optical paths through the cuvettes with the photo-optical examining system at the analysis stations 90.

The cuvette strips 111, 112 are conveniently made by forming a series of shallow, laterally extending depressions along a web of plastic material which is twice the width of a strip 111 or 112 and then cutting along the center-line of the web to form two of the strips 111, 112. The web may be cut and the two strips which are obtained then joined together to form one belt 22 or two webs may first be joined together and then cut along the center-line to form two belts 22. It has been found that by forming the webs using cold molding techniques, optical degradation of the web material is avoided and if the portions of the web which form the side faces 124 of the vessels 24 are restrained during forming to prevent stretching thereof, the optical windows of the resulting vessels are maintained stress-free and with a uniform thickness. Webs of copolyester, such as KODAR brand thermoplastic polyester resin material made by Eastman Kodak Co., or vinyl plastic sheet stock about 0.003 to 0.010 inch thick have been found to provide satisfactory results. In order to facilitate fabrication and assembly of the cuvette belt, the strips may be a laminate having a layer of an easily sealable and biologically inert material such a SURLYN brand inomer resin material manufactured by E. I. DuPont de Nemours & Co., Inc.

Figure 4:
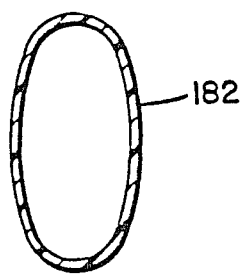
FIG. 4 is a perspective view of a cuvette belt for use in the clinical analyzer of FIG. 1.

While the cuvettes shown in FIGS. 4 and 5 have a generally uniform cross-section, in a preferred cuvette belt for use with the present invention, as shown in FIG. 9, the moths 117 are enlarged in the direction along the belt as explained more fully hereinafter.

The transport 30 comprises a single continuous guide and support track extending through the analyzer having a main tractor belt 32 which engages the indexing holes 26 in the cuvette belt 22 and advances the cuvettes through the instrument at a predetermined rate of advance. A short loading belt 34 threads the cuvette belt 22 into engagement with the main tractor belt 32. The transport 30 advances or indexes the cuvettes through the analyzer 10 in steps corresponding to the spacing between cuvettes (the pitch of the belt) with the cuvettes being stopped and held stationary for a dwell period between each advance. Each step may suitably correspond to a time interval of 5 seconds with a 4 second dwell time between each indexing advance of the cuvettes.

The reagent tablet dispenser carousel 42 comprises a circular array of tabletted reagent dispensers 40 and can be rotated to bring the correct solid reagent dispenser to solid reagent dispensing point "SRD" to drop a single reagent tablet 44 into a cuvette 24. As illustrated, the carousel 42 accommodates thirty-two reagent tablet dispensers 40. It is rotated under microprocessor control to bring the correct tablet dispenser to the dispensing point for each cuvette. The dispensers 40 are detachable and can be loaded randomly. An automatic flagging system indicates when a dispenser is low in tablets.

The diluent and/or liquid reagent dispenser 50 is located adjacent to carousel 42 for adding sufficient diluent 52 for reagent tablet 44 dissolution and/or for dispensing a liquid reagent into the reaction vessel (cuvette) 24 at point "LDD".

The ultrasonic horn 14 acts on the cuvette contents for a sufficient length of time; for example, 45 seconds, to totally dissolve the reagent tablets.

A sample loading and transfer carousel assembly 60 is located downstream of the reagent and diluent dispensers. This carousel assembly comprises a loading carousel 62 into which patient samples 70 are randomly loaded; a transfer carousel 64 which accepts the patient samples 70 from loading carousel 62, identifies the patient sample by means of a bar code reader 66 which reads a bar code label 72 placed on the patient sample container and continuously feeds the patient samples into the system; and finally, an unloading carousel 68 receives the patient samples 70 after testing and stores them in an organized manner in the event that they must later be located and retrieved.

The loading carousel 62 permits continuous random loading of up to 96 patient samples. The transfer carousel 64 continuously feeds patient samples into the system for maximum throughput. Standard collection tubes or micro sample tubes may be accommodated thus allowing utilization of the same containers in which the sample was collected; for example, in the case of blood samples, the 'Vacutainer' tube which is commonly used to draw the serum specimen Sampler 80 for dispensing samples into the cuvettes 24 at point "SD" is located adjacent to transfer carousel 64. This sampler is designed to aspirate about 2 to 20 microliters of patient sample 70 from its container on the transfer carousel and dispense it into a cuvette 24 during the four second dwell period while the cuvette is aligned with the sampler.

The air-jet mixing apparatus 15 (and 15a) according to the invention direct an air jet at an acute angle against the liquid surface in the cuvette adjacent its junction with the cuvette wall to create a vortex thus producing a thorough mixing of the sample with the reagent and diluent. In a preferred embodiment, the apparatus has a fixed, inclined nozzle 150 and the cuvettes 24 are aligned in position beneath the nozzle and the air jet is switched on only during the dwell period when the cuvette is stationary. In order to ensure that the air jet correctly strikes the liquid surface, the liquid level is closely controlled. The structure and operation of preferred embodiments of the air jet mixing apparatus 15 and 15a are described in detail hereinafter.

Figure 3:
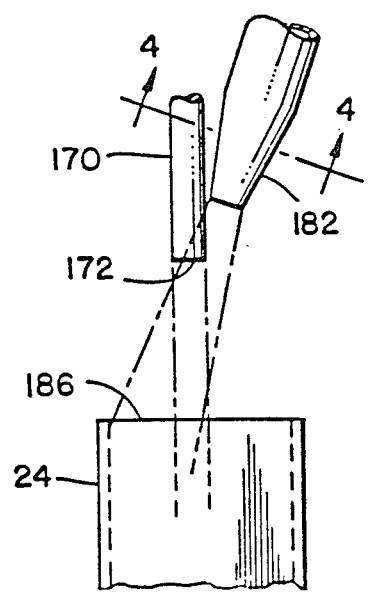
FIG. 3 is a perspective view of a preferred photooptical analysis system used in the clinical analyzer of FIG. 1.

Eight photometric analysis stations 90 are located at points "SA1" through "SA8" along the cuvette track 30. These analysis stations are connected by individual optical guides 92 and 94 to photo-optical system 100. The station "SA1" is arranged following the ultrasonic horn 14 for verifying proper reagent dispensing and dissolution. This system is illustrated in FIG. 3.

The photo-optical system comprises a single light source 101 for generating selected wavelengths of light The output of light source 101 is focused by fixed focusing lens 102 onto the multiple wavelength selective filters disposed about the circumference of rotary source filter wheel 103. The rotation of source filter wheel 103 is regulated by the instrument control microprocessor through double shafted motor 104. The output from source filter wheel 103 is sequentially transmitted through separate light guides 92 to each of the analysis stations.

At the analysis stations, the filtered light energy is passed through the reaction compartment 24 containing the mixture to be analyzed. The output of the analysis stations is then passed back to the photooptical system 100 via separate light guides 94. At this point, a second filter wheel 107, which preferably is identical to and synchronized with source filter wheel 103, intercepts the outputs of light guides 94 before this output is directed to a separate photodetector tube 109 for each analysis station. A reflector 108 may be utilized to focus the output of filter wheel 107 on photodetector tubes 109. In the representation of FIG. 3, only one set of light guides 92, 94 and one photodetector tube 109 is shown for simplicity, although it is to be understood that eight of these elements (one for each analysis station) are required.

The outputs of photodetector tubes 109 are monitored by the control microprocessor and appropriate wavelength output values for each analysis reaction at each analysis station is stored by the microprocessor. When the reaction is completed, the microprocessor will utilize this stored information to calculate the concentration of the selected sample constituent and provide this result to the instrument operator.

As can be seen from FIG. 3, each filter wheel has seven different wavelength selective filters 105 disposed about its circumference. In addition, an opaque blank 106 is located thereon in order to establish the residual "dark current" level of the electronics. Hence, great flexibility is provided by permitting any one or combination of the seven wavelengths to be read at any analysis station for any sample during the four second analysis period. In that filter wheels 103, 107 are rotated at thirty revolutions per second in the preferred embodiment, thirty readings at a particular wavelength may be made each second which can then be averaged to provide a highly accurate final value by the microprocessor.

The second reagent dispenser 54 permits further reaction of the sample to be obtained following initial testing and is shown arranged between analysis stations "SA4" and "SA5". It could be located between any of the analysis stations "SA2" to "SA8". This capacity for optional reagent additions or triggered reaction capability gives added analytical versatility for multiple reagent test situations.

The further air-jet mixing apparatus 15a according to the invention provides for thorough re-mixing of the cuvette contents following addition of further reagent at station 54.

The cuvette sealer 16 seals the tops of the tested cuvettes for convenient clean disposal of completed samples at the cuvette disposal location where they are neatly collected into a lined disposal bin.

The microprocessor control system of the clinical analyzer, which suitably has a 280 processing unit, controls all the operating units thereof in accordance with sample and test information inputted at a suitable operator interface keyboard. In accordance with the desired test results, quantities of a single sample may be dispensed into one or more cuvettes either alone or in combination with any one or more of the solid and liquid reagents and diluent and examined at any one or more of the analysis stations 90. Test results are displayed on a screen and can be printed out.

Turning now to the detailed operation of the instrument system, a phlebotomist draws a patient blood sample 70 which is positively identified by a bar code label 72 placed on the container in which the sample is drawn.

After centrifuging the sample to separate the sera, the sample along with as many others as desired is placed in loading carousel 62 which is then placed into the instrument loading and transfer carousel assembly 60. For emergency stat testing, the patient sample 70 may be loaded directly into one of the empty sample receiving slots 65 of transfer carousel 64, or may be exchanged with a sample container already loaded in transfer carousel 64 prior to bar code reader 66.

The loading carousel is then automatically indexed to a position where the patient sample 70 is transferred into an empty sample receiving slot 65 of transfer carousel 64. The transfer carousel 64 then indexes around to bar code reader 66 which identifies the patient sample. This sample identity is fed to the instrument control microprocessor which correlates this information with the test requisition for this sample that has already been entered into the instrument computer system by the laboratory technician.

The control microprocessor then begins the advance of the cuvette supply reel 20 and belt 22 into cuvette track 30 in response to this sample identification.

This cuvette supply advance is accomplished by the loading belt 34 which threads the cuvette belt into main transport belt 32. If bar code reader 66 detects that there are no further samples to be tested, the control microprocessor will activate cuvette belt cutter 28 which divides cuvette belt 22 into sections 29 having a number of cuvettes corresponding to the number of analysis reactions to be performed at a given time. This procedure minimizes waste for single tests or stat situations. In addition, the cuvette belt cutter 28 may also be periodically operated during continuous operation of the instrument in order to prevent the length of the cuvette belt (which must be disposed of) from becoming unmanageable.

As it is fed into the instrument, the cuvette belt 22 enters a water bath 12 which will maintain the reagent and sample reaction mixture at a predetermined incubation temperature. This reaction temperature is generally either 30 degrees C or 37 degrees C.

For the sake of simplicity, it should also be noted that in FIG. 1 each circular cuvette position point 25 along cuvette track 30 represents a 5 second period.

In other words, every 5 seconds the control microprocessor will step a particular cuvette reaction compartment 24 to the next circular position along the cuvette track 30.

During the time that the transfer carousel 64 is indexing the sample 70 between the bar code reader 66 and its position where sampler 80 aspirates a portion thereof, an appropriate reagent is added at either point "SRD" or "LDD" to the reaction compartment that is timed by the control microprocessor to receive the sample. The microprocessor causes the proper reagent to be dispensed from one of the thirty-two different tabletted reagent dispensers 40 that can be accommodated by dispenser carousel 42, or the multiple liquid reagents that can be accommodated by diluent/liquid reagent dispenser 50, in response to the patient sample identification by bar code reader 66.

If a tabletted reagent is dispensed, sufficient diluent for tablet dissolution is added thereto at point "LDD" and an ultrasonic horn 14 is utilized to provide 45 seconds of high energy ultra-sound to completely break up and dissolve the reagent tablet. In the preferred embodiment, this reagent mixture has a volume of 200 microliters.

After this reconstitution of the reagent in the predetermined amount of diluent, the reaction compartment is passed to a reagent quality control analysis station at point "SA1". Here, each reagent mixture is photometrically analyzed to verify proper reagent dispensing and dissolution. Furthermore, the microprocessor can also utilize this reading to adjust for any minor variation in reagent amount and resulting concentration that may exist from tablet to tablet.

Next, the reaction compartment 24 is transported to point "SD" where sampler 80 will dispense the appropriate patient sample into the reaction compartment 24. As noted above, the main transport belt 32 of cuvette track 30 is carefully synchronized with the reagent dispensers and the sample to insure that the proper reaction mixture is obtained as ordered by the control microprocessor. Since sampler 80 is the only non-discrete element of the analysis system, its probe is flushed with additional diluent to prevent contamination and carry-over between samples. In the preferred embodiment, the final reaction volume is 300 microliters. Following addition of the sample, the contents of the cuvette are thoroughly mixed at air-jet mixing station 15 which is described in detail hereinbelow.

The next analysis station is the sample blanking station located at point "SA2". It has been found desirable to dispense an amount of each patient sample into a reaction compartment without a reagent being added to obtain a sample blank. This sample blank value may be obtained at this analysis station or any of the following six analysis stations as required.

The second reagent dispenser 54 is located further down the cuvette track 30 for multiple or triggered reaction capability. For example, such a reagent dispenser would be useful in conducting CKMB constituent analysis. The further air-jet mixing station 15a provides thorough mixing of the cuvette contents following this addition.

At the end of the cuvette track 30, the cuvette sealer 16 is located to seal the tops of the cuvette reaction compartments after testing for convenient and sanitary disposal of the samples. After passing through the cuvette sealer 16, the cuvette belt 22 is stripped off of the main transport belt 32 by an unloading belt 36 which removes the tested cuvettes from the water bath 12 and automatically discards them into disposal bin 18.

Turning now to FIGS. 6 to 11, embodiments of mixing apparatus according to the invention suitable for use on the above-described automated clinical analyzer 10 at mixing stations 15 and 15a will now be described. FIG. 6 shows an embodiment of mixing apparatus 15 comprising a nozzle 150 arranged above the path of the cuvettes 24 with which the cuvettes are aligned in turn so that the nozzle is directed at an acute angle at the junction between the surface of the liquid in the cuvette and the wall of the cuvette. The nozzle 150 is fixed in position. In order to insure that the air-jet J produced thereby is properly coordinated with the liquid surface in the cuvette so that it strikes the surface at the junction thereof with the cuvette wall, the quantities of reagent, diluent and sample are closely controlled so that the liquid in all the cuvettes is at a constant preset level. (One exception to this is where the sample is dispensed into a cuvette alone for sample blanking and mixing is not required.)

The nozzle 150 is mounted on a frame 151 so that its orifice is just above the tops of the cuvettes with sufficient clearance to avoid interference with the cuvettes as they are advanced. It may, for example, be about 0.7 mm above the tops of the cuvettes. While the nozzle is fixed in position during use the frame 151 may incorporate means for adjusting the angle of the nozzle either manually or automatically during set-up or between runs. A valve 152 is provided for controlling the supply of air to the nozzle 150 from an air supply 153 to which it is connected by an air line 154. Operation of the valve 152 is by means of a controller 155 connected to the analyzer's microprocessor.

As explained above, the cuvettes are indexed stepwise through the analyzer along track 30 and each cuvette is positioned stationarily in alignment beneath the orifice of the nozzle 150 during the dwell period between advancing steps. Activation of the air jet J is limited to this dwell period so that the cuvettes are stationary during mixing.

It has been found that by directing the air jet J at an acute angle at the junction of the liquid surface in the cuvette with the cuvette wall, perferably so that it hits the meniscus at this junction, a vortex is created which produces a thorough mixing of the contents of the cuvette. This mixing is such that even a reagent which is particularly immiscible in the diluent becomes totally suspended within the diluent and the reaction between the reagent and the sample is more complete and rapidly achieved. FIG. 10 shows a representative pattern of such mixing within the cuvette by the air jet J, however, the exact pattern of mixing taken by the material may be any suitable one. By ensuring that the air jet hits the liquid surface in the meniscus area, it has been found that very good mixing within the material is achieved. During such mixing, it is seen that the materials climb the wall of the cuvette opposite the point where the air jet strikes the liquid surface. This is depicted by the dotted swirling action behind the air jet at the righthand side of the cuvette in FIG. 10. The use of an air jet to mix the contents of the cuvette in the manner described has been found to work surprisingly well considering the relatively small amount of fluid being mixed and the relatively small confines of the cuvette in which the mixing has to take place.

It has been found that arranging the air jet J at an acute angle as possible so that the horizontal components of the air jet are maximized produces the most beneficial results. In the embodiment of FIGS. 6 to 8, the angle of the air jet is limited by the level of the liquid in the cuvette which is itself limited by the need to avoid the contents splashing out of the cuvette during mixing. In order to maximize the inclination of the air jet, the nozzle 150 is arranged just above the cuvette diametrically opposite the point at which the air jet strikes the liquid surface.

In the embodiment illustrated, the cuvettes are generally rectangular in cross-section with their longer dimension extending along the length of the cuvette belt. In order to maximize the inclination of the air jet, the nozzle 150 is as shown in FIG. 8 directed along the longer cross-sectional dimension of the cuvette. Another way of maximizing the angle of inclination of the air jet is shown in FIG. 9 which illustrates a modified form of cuvette particularly suitable for use with the present invention which has the mouth of the cuvette enlarged in the dimension along the length of the cuvette belt.

In still one other embodiment, the air jet of the nozzle can be aligned along the longer cross-sectional dimension of the cuvette and coincident with the longer inside surface of the cuvette. In this manner, a larger area of meniscus may be affected by the jet thereby further enhancing the mixing action.

It has been found that the preferred angle of inclination of the air jet to the liquid surface may vary between about 75 degrees and about 80 degrees with best results at about 75.5 degrees while the distance between the mouth of the cuvette and the liquid level varies between about 15 mm and about 25 mm. This is when the cuvette is arranged vertically.

It will be understood that the pressure of the air jet is also a factor which affects mixing and splashing.

The actual air jet pressure will vary depending upon the height of the nozzle above the top of the fluid in the cuvette. In an embodiment disclosed herein, for example, wherein the nozzle is about 0.030 inches, above the fluid top level, it has been found that an air jet pressure of between about 2 psi and about 3 psi is adequate. Such a pressure may be achieved using simple 'air dryer' or 'aquarium' or like type of pump.

In a preferred embodiment in which the cross-sectional dimension of the cuvette along which the air jet is directed is about 5.1 mm, the nozzle is inclined at an angle of degrees to the cuvette and the cuvette contains 300 microliters of materials defining a liquid level which is about 20.6 mm below the mouth of the cuvette while the air jet pressure is about 2.5 psi.

While the mixing time of 4 seconds has been found effective for use in the embodiment described above, the time period may vary, for example, between about 3.5 seconds and about 4.5 seconds depending upon the materials to be mixed and the other parameters described above. In this embodiment, the air jet is activated continuously over such time period. In operation, the cuvettes 24 are advanced in turn into position beneath the nozzle 150 in alignment therewith which is closely controlled by the tractor belt 32. The microprocessor, which has al ready closely controlled the quantities of materials dispensed into the cuvette to the preset liquid level, directs the air jet at the meniscus at the junction between the liquid surface and the cuvette wall to create a vortex which produces a thorough mixing of the contents of the cuvette. At the end of the dwell period, the air jet is switched off and the cuvette belt is advanced to bring the next cuvette into stationary position beneath the nozzle when the mixing process is repeated.

The mixing apparatus 15a, which is arranged after the further reagent dispenser 54, is identical to the apparatus 15 but the nozzle can be inclined at a slightly shallower (more horizontal) angle since the liquid level will be slightly greater due to the addition of further reagent.

In the embodiment described above, the air-jet nozzle 150 is non-invasive of the cuvette, thus maximizing throughput. However, in a modification as shown in FIG. 11, the nozzle is inserted into the cuvette during mixing. This has the effect of limiting throughput and may result in contamination of the nozzle which can be dealt with by flushing the nozzle with diluent between mixing operations. However, it does produce a system in which the angle of inclination of the nozzle is not limited by the geometry of the cuvette so that it can be inclined more nearly to the horizontal thus desirably maximizing the horizontal component of the air jet. In this embodiment, the nozzle 150 has a dog-leg bend in it and it is mounted on an elevator mechanism schematically represented at 160 by which it can be raised and lowered between a lowered, operative position as shown in solid outline and a raised, inoperative position as shown in dotted outline for cuvette indexing. With this arrangement the air jet angle can be reduced to as little as 8 degrees to the liquid surface (horizontal). An angle of between about 8 degrees and about 15 degrees to the horizontal is preferred. As in the previous embodiment, the air jet is directed at the junction between the liquid surface and the cuvette wall.

The height of the nozzle above the liquid surface is to some extent determined by the angle of the air jet it produces, but when it is sufficiently close to the liquid surface that it becomes contaminated by splashing, it is cleaned between mixing operations.

Although particular configurations and features of the present invention have been discussed in connection with the above-described preferred embodiments thereof, it should be understood that those skilled in the art may make various changes, modifications and substitutions thereto without departing from the spirit and scope of the invention as defined in the appended claims.

For example, while in the embodiment shown in FIGS. 6 to 8, the nozzle 150 is fixed in position during an operational sequence, it may be adjustable automatically to accommodate different liquid levels and/or cuvette sizes. Thus, its angle of inclination may be variable automatically within limits to accommodate different liquid levels in response to a liquid level sensor.

Also, in the embodiment illustrated in FIGS. 6 to 8, the orifice of the air jet is arranged just above the wall of the cuvette diametrically opposite where the air jet strikes the cuvette contents. It will be understood however that the orifice may be arranged out-of-line with the mouth of the cuvette as long as the air jet clears the wall of the cuvette at this point.

Although the nozzle 150 is shown aligned with the direction of advance of the cuvette belt, it will be understood that it may be oriented in other directions.

One recurring problem with the system described above which has been noted, addressed, and solved concerns possible contamination of successive cuvettes 24. The particular problem manifested itself as reagent from one cuvette being carried via a sample probe 170 of the sampler 80 into the next adjacent cuvette in the train as illustrated in FIGS. 1 & 12. Because of the nature of the reactants in the individual chemistries, there are chemical incompatibilities, constituents from one chemistry or chemical poisons for the reaction which is occurring in an adjacent chemistry. In any event, it was a totally unacceptable situation.

Either grossly elevated values or grossly depressed values could result, or falsely depressed or falsely elevated values because of very minute degrees of carryover. Carryover could even be measured beyond the next adjacent cuvette. While a variety of other devices and methods were attempted, the apparatus illustrated in FIGS. 12-15 has proved to be excellent for the purposes of the invention.

As previously noted, a single reagent tablet 44 is dispensed into a cuvette 24 at point "SRD". Thereafter, diluent such as pure water, in an approximate amount of 22 microliters is dispensed into the cuvette 24 at point "LDD". Thereupon, the sample probe 170 of the sampler 80 is positioned (FIG. 2) so as to draw up or aspirate a sample amount which may be on the order of 10 microliters. The sample probe 170 thereupon moves into position over the next occurring cuvette 24 being advanced through the system. In the customary fashion, a tip 172 of the sample probe 170 descends into the cuvette. However, the mechanism operating the sample probe 170 assures that the tip 172 does not descend a sufficient distance into the cuvette to come into contact with the liquid therein. The sample or specimen material is then dispensed into the reagent and diluent solution within the cuvette, followed by an additional amount of diluent which serves to flush the remains of the sample material within the sample probe 170. While the average volume of a specimen of sample material is approximately 10 microliters, a typical range of volumes is 2-20 microliters. Sufficient diluent is then added to the mixture so that the final volume in the cuvette is approximately 300 microliters. This amount typically includes the positive displacement of the reagent tablet.

A problem can arise, however, with the system just described in that following the diluent dispensing step, it frequently occurs that a drop of the diluent remains on the probe 170 at its tip 172 by reason of capillary attraction. That is, if the droplet were to descend into the fluid mixture within the cuvette, any volumetric error would be minimal and could readily be accommodated. This is for the reason that the size of the drop would be typically on the order of 1-2 microliters while the cuvette has approximately 300 microliters of liquid al ready in it. Thus, any volumetric error would be substantially less than 1%.

A real problem, however, occurred as the sample probe 170 returned to aspirate its next sample from a sample container 65. As the probe 170 descended into the sample container, the drop resting at the tip 170 would fall off into the sample container which typically contains an amount of sample material in the range of 50-500 microliters. If the probe were only to return to the sample container on one occasion, a volumetric error generally on the order just discussed with respect to the cuvette would occur and could be accommodated. However, it is not unusual in practice using the Paramax Analytical System to perform 30 or more tests on the sample material in a patient sample 70. Therefore, if a drop has a volume of approximately 2 microliters and 30 tests are being performed, that results in a total of 60 microliters diluting a sample container which typically averages about 200 microliters, effectively causing a 30% dilution of the patient sample. Such a dilution is beyond the range which can properly be accommodated while still providing accurate results.

To correct this problem, the Paramax Analytical System has been modified to include the improvement generally described in FIGS. 12-15. Thus, a support bracket 178 is suitably mounted on frame structure 180 of the machine in the region of the sampler 80. The bracket 178 serves to support in a suitable fashion an air nozzle 182 which, in turn, is attached to a supply line 184 of pressurized air.

The bracket 178 supports the air nozzle 182 so that it is directed downwardly and at an angle toward a mouth 186 of the cuvette. A desirable angle between a longitudinal axis of the air nozzle and a longitudinal or vertical axis of the cuvette 224 is 40 degrees, although a broad range of angles could satisfy the invention.

As the sample probe 170 dispenses first the sample material and then an additional charge of diluent into the cuvette 24, it is then withdrawn from the cuvette such that the tip 172 passes within the path of a stream of air which issues from the air nozzle 182. While the nozzle remains stationary, the probe tip 172 moves across the plane of the air and in effect, actually wipes the surface of the probe 170 at the tip 172, blowing the residual droplets of diluent into the cuvette 24. As seen particularly in FIG. 15, the nozzle 182 preferably has an opening of elliptical shape whose major axis is parallel with the cuvette train.

To illustrate the effectiveness of the invention, carryover type testing was performed using a chloride reagent which has a very high concentration of iron. It has fortified cyanide in it. Several chloride tests were performed with this high iron concentration followed by several iron tests. Iron, unlike most of the anolate chemistries measures in microgram quantities rather than milligram quantities. As a result, using this technique, it is possible to measure down to as little as two nanoliters of carryover. Five separate runs, each of four to five hours in duration utilizing this carryover detecting arrangement resulted in no detectable carryover. In each instance, the first iron detected immediately following the chloride had the same value or is of the same population as the iron values following it. This was convincing evidence that no carryover results when the system of the invention is utilized.

While the systems described above are automated, it will be understood that in other systems a cuvette may be positioned manually beneath the nozzle or inserted over the nozzle.

It should be understood that the above described embodiments of the invention are illustrative only and that modifications thereof may occur to those skilled in the art. Accordingly, this invention is not to be regarded as limited to the embodiments disclosed herein, but is to be limited only as defined by the appended claims.

I claim:

1. A method of avoiding contamination and dilution of sample in the course of analyzing a biological sample where multiple aliquot are taken from the biological sample comprising the steps of:

dispensing from the tip end of a tubular sample probe a sample material into a cuvette with a reagent material and diluent to partially fill the cuvette without permitting the sample probe to contact the reagent material;

while the tip end of the sample probe remains positioned above the cuvette, flushing the interior of the sample probe after the sample material has been dispensed into the cuvette with an amount of diluent sufficient to adjust the contents of the cuvette to a predetermined volume;

withdrawing the sample probe from the cuvette; and directing a stream of air at the sample probe during the withdrawing step such that the tip end of the sample probe passes through the air stream to eject therefrom and into the cuvette any diluent remaining on the tip end.

2. A method as set forth in claim 1 wherein the stream of air is directed downwardly and at an angle toward the open end of the cuvette.

3. A method as set forth in claim 2 wherein the angle between the sample probe and the stream of air directed at the tip and end is approximately 40 degrees.

4. Apparatus for analyzing liquid biological samples comprising:

a container for containing sample material to be analyzed;

a cuvette adapted to receive a reagent used for analyzing the sample material;

a tubular sample probe having a tip end movable between a first position for withdrawing sample material from said sample container and a second position for dispensing sample material through said tip end into said cuvette;

means for moving said sample probe between said first and second positions;

means for flushing the interior of said sample probe into said cuvette after sample material has been dispensed therefrom with a diluent to adjust the contents of the cuvette to a predetermined volume; and means for directing a stream of air at the sample probe such that said tip end passes through the steam of air to eject therefrom into said cuvette any diluent remaining thereon before said sample probe returns to the first position.

5. Apparatus as set forth in claim 4 wherein:
said directing means is a nozzle having a longitudinal axis directed downwardly and at an angle toward the open end of said cuvette.

6. Apparatus for analyzing liquid biological samples comprising:

a cuvette adapted to receive a reagent used for analyzing the sample material;

a tubular sample probe having a tip end movable between a first position for withdrawing sample material from a sample container and a second position for dispensing sample material through said tip end into said cuvette;

means for moving said sample probe between said first and second positions means for flushing the interior of said sample probe after sample material has been dispensed therefrom and while said tip end remains positioned above the cuvette with a diluent to adjust the contents of the cuvette to a predetermined volume; and means for directing a stream of air at said sample probe such that said tip end of said sample probe passes through said steam of air to eject therefrom any diluent remaining thereon while said tip end remains positioned above the cuvette.

7. Apparatus as set forth in claim 6 wherein said directing means is a nozzle having a longitudinal axis directed at the open end of the cuvette.

8. Apparatus as set forth in claim 7 wherein the longitudinal axis of said nozzle is directed downwardly and at an angle toward the open end of the cuvette.

9. Apparatus as set forth in claim 7 wherein said nozzle has means defining an opening of elliptical shape whose major axis is substantially horizontal.

10. Apparatus as set forth in claim 6 including transport means for moving said tip end of said sample probe between a first position for withdrawing sample material from a sample container and a second position for dispensing sample material into the cuvette.

* * * * *